(12) United States Patent
Chen et al.

(10) Patent No.: US 10,707,886 B2
(45) Date of Patent: Jul. 7, 2020

(54) ASYNCHRONOUS SUCCESSIVE APPROXIMATION ANALOG-TO-DIGITAL CONVERTER AND RELATED METHODS AND APPARATUS

(71) Applicant: Butterfly Network, Inc., Guilford, CT (US)

(72) Inventors: Kailiang Chen, Branford, CT (US); Tyler S. Ralston, Clinton, CT (US)

(73) Assignee: Butterfly Network, Inc., Guilford, CT (US)

( * ) Notice: Subject to any disclaimer, the term of this patent is extended or adjusted under 35 U.S.C. 154(b) by 0 days.

(21) Appl. No.: 16/392,325

(22) Filed: Apr. 23, 2019

(65) Prior Publication Data
US 2019/0253061 A1   Aug. 15, 2019

Related U.S. Application Data

(63) Continuation of application No. 15/979,883, filed on May 15, 2018, now Pat. No. 10,277,236, which is a
(Continued)

(51) Int. Cl.
*H03M 1/12* (2006.01)
*H03M 1/00* (2006.01)
(Continued)

(52) U.S. Cl.
CPC .......... *H03M 1/002* (2013.01); *A61B 8/4494* (2013.01); *H03M 1/125* (2013.01); *H03M 1/462* (2013.01); *A61B 8/4483* (2013.01); *A61B 8/54* (2013.01)

(58) Field of Classification Search
CPC ...... H03M 1/002; H03M 1/125; A61B 8/4494
(Continued)

(56) References Cited

U.S. PATENT DOCUMENTS 5,640,433 A   6/1997   Szczebak et al.
5,844,445 A   12/1998   Takeyari
(Continued)

FOREIGN PATENT DOCUMENTS

CN   103607130 A    2/2014
EP   1 932 479 A1   6/2008
(Continued)

OTHER PUBLICATIONS

PCT/US2016/064406, Feb. 17, 2017, International Search Report and Written Opinion.
(Continued)

*Primary Examiner* — Peguy Jean Pierre
(74) *Attorney, Agent, or Firm* — Wolf, Greenfield & Sacks, P.C.

(57) ABSTRACT

An ultrasound device including an asynchronous successive approximation analog-to-digital converter and method are provided. The device includes at least one ultrasonic transducer, a plurality of asynchronous successive-approximation-register (SAR) analog-to-digital converters (ADC) coupled to the at least one ultrasonic transducer, at least one asynchronous SAR in the plurality having a sample and hold stage, a digital-to-analog converter (DAC), a comparator, and control circuitry, wherein a DAC update event following at least one bit conversion is synchronized to a corresponding DAC update event of at least one other ADC in the plurality of ADCs.

12 Claims, 5 Drawing Sheets

Related U.S. Application Data continuation of application No. 15/605,469, filed on May 25, 2017, now Pat. No. 10,014,871, which is a continuation of application No. 14/957,418, filed on Dec. 2, 2015, now Pat. No. 9,705,518.

(51) Int. Cl.
*A61B 8/00* (2006.01)
*H03M 1/46* (2006.01)

(58) Field of Classification Search
USPC .............................................. 341/155, 156
See application file for complete search history.

(56) References Cited

U.S. PATENT DOCUMENTS

| | | | |
|---|---|---|---|
| 7,313,053 | B2 | 12/2007 | Wodnicki |
| 7,353,417 | B2* | 4/2008 | Desuche ............. G06F 15/7814 341/148 |
| 8,766,721 | B1 | 7/2014 | Dusad |
| 8,852,103 | B2 | 10/2014 | Rothberg et al. |
| 8,957,802 | B1 | 2/2015 | Evans |
| 9,071,265 | B1 | 6/2015 | Dey et al. |
| 9,112,521 | B2 | 8/2015 | Dedic et al. |
| 9,229,097 | B2 | 1/2016 | Rothberg et al. |
| 9,369,140 | B1 | 6/2016 | Sundaresan et al. |
| 9,473,136 | B1 | 10/2016 | Chen et al. |
| 9,492,144 | B1 | 11/2016 | Chen et al. |
| 9,705,518 | B2 | 7/2017 | Chen et al. |
| 9,871,529 | B1* | 1/2018 | Chong .................... H03M 1/38 |
| 9,933,516 | B2 | 4/2018 | Chen et al. |
| 9,958,537 | B2 | 5/2018 | Chen et al. |
| 10,014,871 | B2 | 7/2018 | Chen et al. |
| 10,050,639 | B1 | 8/2018 | Berens et al. |
| 10,277,236 | B2 | 4/2019 | Chen et al. |
| 2005/0203392 | A1 | 9/2005 | Petersen et al. |
| 2007/0001764 | A1 | 1/2007 | Huang et al. |
| 2007/0242567 | A1 | 10/2007 | Daft et al. |
| 2009/0140810 | A1 | 6/2009 | Kim et al. |
| 2009/0250729 | A1 | 10/2009 | Lemmerhirt et al. |
| 2009/0289716 | A1 | 11/2009 | Jaeger et al. |
| 2010/0039305 | A1 | 2/2010 | Yoshioka |
| 2010/0152587 | A1 | 6/2010 | Haider et al. |
| 2010/0305449 | A1 | 12/2010 | Wegener et al. |
| 2010/0317972 | A1 | 12/2010 | Baumgartner et al. |
| 2011/0050634 | A1 | 3/2011 | Lin et al. |
| 2011/0057823 | A1 | 3/2011 | Harpe |
| 2012/0262221 | A1 | 10/2012 | Bottarel et al. |
| 2013/0069807 | A1 | 3/2013 | Sestok et al. |
| 2013/0187697 | A1 | 7/2013 | Choy et al. |
| 2014/0070972 | A1 | 3/2014 | Morgado et al. |
| 2014/0078866 | A1 | 3/2014 | Kanamori et al. |
| 2014/0288428 | A1 | 9/2014 | Rothberg et al. |
| 2015/0032002 | A1 | 1/2015 | Rothberg et al. |
| 2015/0171879 | A1 | 6/2015 | Kimura et al. |
| 2015/0263756 | A1 | 9/2015 | Chiu et al. |
| 2015/0280728 | A1 | 10/2015 | Singh et al. |
| 2015/0297193 | A1 | 10/2015 | Rothberg et al. |
| 2016/0056830 | A1 | 9/2016 | Malik et al. |
| 2017/0160239 | A1 | 6/2017 | Chen et al. |
| 2017/0160387 | A1 | 6/2017 | Chen et al. |
| 2017/0160388 | A1 | 6/2017 | Chen et al. |
| 2017/0163225 | A1 | 6/2017 | Chen et al. |
| 2017/0163276 | A1 | 6/2017 | Chen et al. |
| 2017/0202541 | A1 | 7/2017 | Ralston |
| 2017/0264307 | A1 | 9/2017 | Chen et al. |
| 2017/0307739 | A1 | 10/2017 | Chen et al. |
| 2018/0262200 | A1 | 9/2018 | Chen et al. |
| 2019/0086525 | A1 | 3/2019 | Chen et al. |
| 2019/0140603 | A1 | 5/2019 | Chen et al. |

FOREIGN PATENT DOCUMENTS

| | | |
|---|---|---|
| FR | 2 726 408 A1 | 5/1996 |
| JP | 2002-125969 A | 5/2002 |
| JP | 2010-022761 A | 2/2010 |
| JP | 2010-042146 A | 2/2010 |
| JP | 2010068444 A | 3/2010 |
| JP | 2010-167167 A | 8/2010 |
| JP | 2010-193329 A | 9/2010 |
| JP | 2012-528685 A | 11/2012 |
| JP | 2015-033123 A | 2/2015 |
| JP | 2015-056890 A | 3/2015 |
| JP | 2015-115883 A | 6/2015 |
| KR | 20120006351 A | 1/2012 |
| TW | 201445554 A | 12/2014 |

OTHER PUBLICATIONS

PCT/US2016/064406, Jun. 14, 2018, International Preliminary Report on Patentability.
EP 16871486.3, Jun. 18, 2019, Extended European Search Report.
EP 16871492.1, Jul. 18, 2019, Extended European Search Report.
EP 16871500.1, Jun. 17, 2019, Extended European Search Report.
EP 16871466.5, May 28, 2019, Extended European Search Report.
EP 16871463.2, Jun. 4, 2019, Extended European Search Report.
International Search Report and Written Opinion dated Feb. 17, 2017 for Application No. PCT/US2016/064406.
International Preliminary Report on Patentability dated Jun. 14, 2018 in connection with International Application No. PCT/US2016/064406.
Extended European Search Report dated Jun. 18, 2019 in connection with European Application No. 16871486.3.
Extended European Search Report dated Jul. 18, 2019 in connection with European Application No. 16871492.1.
Extended European Search Report dated Jun. 17, 2019 in connection with European Application No. 16871500.1.
Extended European Search Report dated May 28, 2019 in connection with European Application No. 16871466.5.
Extended European Search Report dated Jun. 4, 2019 in connection with European Application No. 16871463.2.
Taiwanese Office Action dated Jan. 19, 2018 in connection with Taiwanese Application No. 105139662.
Agarwal et al., Single-Chip Solution for Ultrasound Imaging Systems: Initial Results. 2007 IEEE Ultrasonics Symposium. Oct. 1, 2007;1563-6.
Chen et al., Ultrasonic Imaging Front-End Design for CMUT: A 3-Level 30Vpp Pulse-Shaping Pulser with Improved Efficiency and a Noise-Optimized Receiver. IEEE Asian Solid-State Circuits Conference. Nov. 12-14, 2012;173-6.
Cheng et al., An Efficient Electrical Addressing Method Using Through-Wafer Vias for Two-Dimensional Ultrasonic Arrays. 2000 IEEE Ultrasonics Symposium. 2000;2:1179-82.
Cheng et al., CMUT-in-CMOS ultrasonic transducer arrays with on-chip electronics. Transducers 2009. IEEE. Jun. 21, 2009;1222-5.
Cheng et al., Electrical Through-Wafer Interconnects with Sub-PicoFarad Parasitic Capacitance. 2001 Microelectromechan Syst Conf. Aug. 24, 2001;18-21.
Daft et al., 5F-3 A Matrix Transducer Design with Improved Image Quality and Acquisition Rate. 2007 IEEE Ultrasonics Symposium. Oct. 1, 2007;411-5.
Daft et al., Microfabricated Ultrasonic Transducers Monolithically Integrated with High Voltage Electronics. 2004 IEEE Ultrasonics Symposium. Aug. 23, 2004;1:493-6.
Gurun et al., Front-end CMOS electronics for monolithic integration with CMUT arrays: circuit design and initial experimental results. Proc Ultrason Symp. 2008;390-3.
Khuri-Yakub et al., Miniaturized Ultrasound Imaging Probes Enabled by CMUT Arrays with Integrated Frontend Electronic Circuits. Conf Proc IEEE Eng Med Biol Soc. 2010;1:5987-90. doi:10.1109/IEMBS.2010.5627580. Epub Dec. 6, 2010. 13 pages.
Kim et al., Design and Test of a Fully Controllable 64×128 2-D CMUT Array Integrated with Reconfigurable Frontend ASICs for Volumetric Ultrasound Imaging. IEEE. International Ultrasonics Symposium Proceedings. Oct. 7-10, 2012;77-80. doi: 10.1109/ULTSYM.2012.0019.

(56) References Cited

OTHER PUBLICATIONS

Reyes et al., A 2GS/s 6-bit CMOS time-interleaved ADC for analysis of mixed-signal calibration techniques. Analog Integrated Circuits and Signal Processing. Springer New York LLC. Jul. 3, 2015; 85(1):3-16.

Um et al., 24.8 An Analog-digital-hybrid single-chip RX beamformer with non-uniform sampling for 2D-CMUT ultrasound imaging to achieve wide dynamic range of delay and small chip area. IEEE International Solid State Circuits Conference. IEEE Service Center. Feb. 9, 2014; pp. 427-7.

\* cited by examiner

ASYNCHRONOUS SUCCESSIVE APPROXIMATION ANALOG-TO-DIGITAL CONVERTER AND RELATED METHODS AND APPARATUS

RELATED APPLICATIONS

This Application is a Continuation claiming the benefit under 35 U.S.C. § 120 of U.S. application Ser. No. 15/979,883, filed May 15, 2018 under entitled "ASYNCHRONOUS SUCCESSIVE APPROXIMATION ANALOG-TO-DIGITAL CONVERTER AND RELATED METHODS AND APPARATUS," which is hereby incorporated herein by reference in its entirety.

application Ser. No. 15/979,883 is a Continuation claiming the benefit under 35 U.S.C. § 120 of U.S. application Ser. No. 15/605,469, filed May 25, 2017 under entitled "ASYNCHRONOUS SUCCESSIVE APPROXIMATION ANALOG-TO-DIGITAL CONVERTER AND RELATED METHODS AND APPARATUS," which is hereby incorporated herein by reference in its entirety.

U.S. patent application Ser. No. 15/605,469 is a Continuation claiming the benefit under 35 U.S.C. § 120 of U.S. patent application Ser. No. 14/957,418, filed Dec. 2, 2015 under entitled "ASYNCHRONOUS SUCCESSIVE APPROXIMATION ANALOG-TO-DIGITAL CONVERTER AND RELATED METHODS AND APPARATUS," which is hereby incorporated herein by reference in its entirety.

BACKGROUND

Field

The present application relates to ultrasound devices having a successive approximation analog-to-digital converter.

Related Art

Ultrasound devices may be used to perform diagnostic imaging and/or treatment. Ultrasound imaging may be used to see internal soft tissue body structures. Ultrasound imaging may be used to find a source of a disease or to exclude any pathology. Ultrasound devices use sound waves with frequencies which are higher than those audible to humans. Ultrasonic images are made by sending pulses of ultrasound into tissue using a probe. The sound waves are reflected off the tissue, with different tissues reflecting varying degrees of sound. These reflected sound waves may be recorded and displayed as an image to the operator. The strength (amplitude) of the sound signal and the time it takes for the wave to travel through the body provide information used to produce an image.

Many different types of images can be formed using ultrasound devices. The images can be real-time images. For example, images can be generated that show two-dimensional cross-sections of tissue, blood flow, motion of tissue over time, the location of blood, the presence of specific molecules, the stiffness of tissue, or the anatomy of a three-dimensional region.

SUMMARY

According to an aspect of the present application, there is provided an apparatus, comprising at least one ultrasonic transducer, a plurality of asynchronous successive-approximation-register (SAR) analog-to-digital converters (ADC) coupled to the at least one ultrasonic transducer, at least one asynchronous SAR in the plurality having a sample and hold stage, a digital-to-analog converter (DAC), a comparator, and control circuitry, wherein a DAC update event following at least one bit conversion is synchronized to a corresponding DAC update event of at least one other ADC in the plurality of ADCs.

According to an aspect of the present invention, there is provided a method of operating an ultrasound device having a plurality of ultrasonic transducers and a plurality of asynchronous successive-approximation-register (SAR) analog-to-digital converters (ADC), each ultrasound transducer being respectively coupled to an ADC, each asynchronous SAR in the plurality having a sample and hold stage, a digital-to-analog converter (DAC), a comparator, and control circuitry, the method including converting, in response to a first clock signal, a first bit of one ADC, updating a DAC in the one ADC in response to the converting; and updating a DAC in another ADC in the plurality of ADCs in response to the updating a DAC in the one ADC.

BRIEF DESCRIPTION OF THE DRAWINGS

Various aspects and embodiments of the application will be described with reference to the following figures. It should be appreciated that the figures are not necessarily drawn to scale. Items appearing in multiple figures are indicated by the same reference number in all the figures in which they appear.

DETAILED DESCRIPTION

The inventors have recognized and appreciated that the power consumption associated with analog-to-digital converters may be greatly improved by removing the need for power-hungry high-speed clock circuits.

Aspects of the present application relate to an asynchronous successive approximation analog-to-digital converter (ADC) that does not require the use of high-speed clock signals to govern the timing associated with the successive conversion. Accordingly, each iteration of the successive conversion process may be triggered by the completion of the previous iteration.

Furthermore, the inventors have recognized and appreciated that the speed associated with analog-to-digital converters may be greatly improved by removing the need for time-constraining clock circuits. The conversion speed of typical analog-to-digital converters is limited by the repetition rate of the clock signal used to time the circuit.

Aspects of the present application relate to an asynchronous successive approximation analog-to-digital converter (ADC) that does not require the use of high-speed clock signals to govern the timing associated with the successive conversion. Accordingly, the conversion speed may be solely limited by the delay caused by the circuitry necessary to perform the conversion.

The aspects and embodiments described above, as well as additional aspects and embodiments, are described further below. These aspects and/or embodiments may be used individually, all together, or in any combination of two or more, as the application is not limited in this respect.

Figure 1:
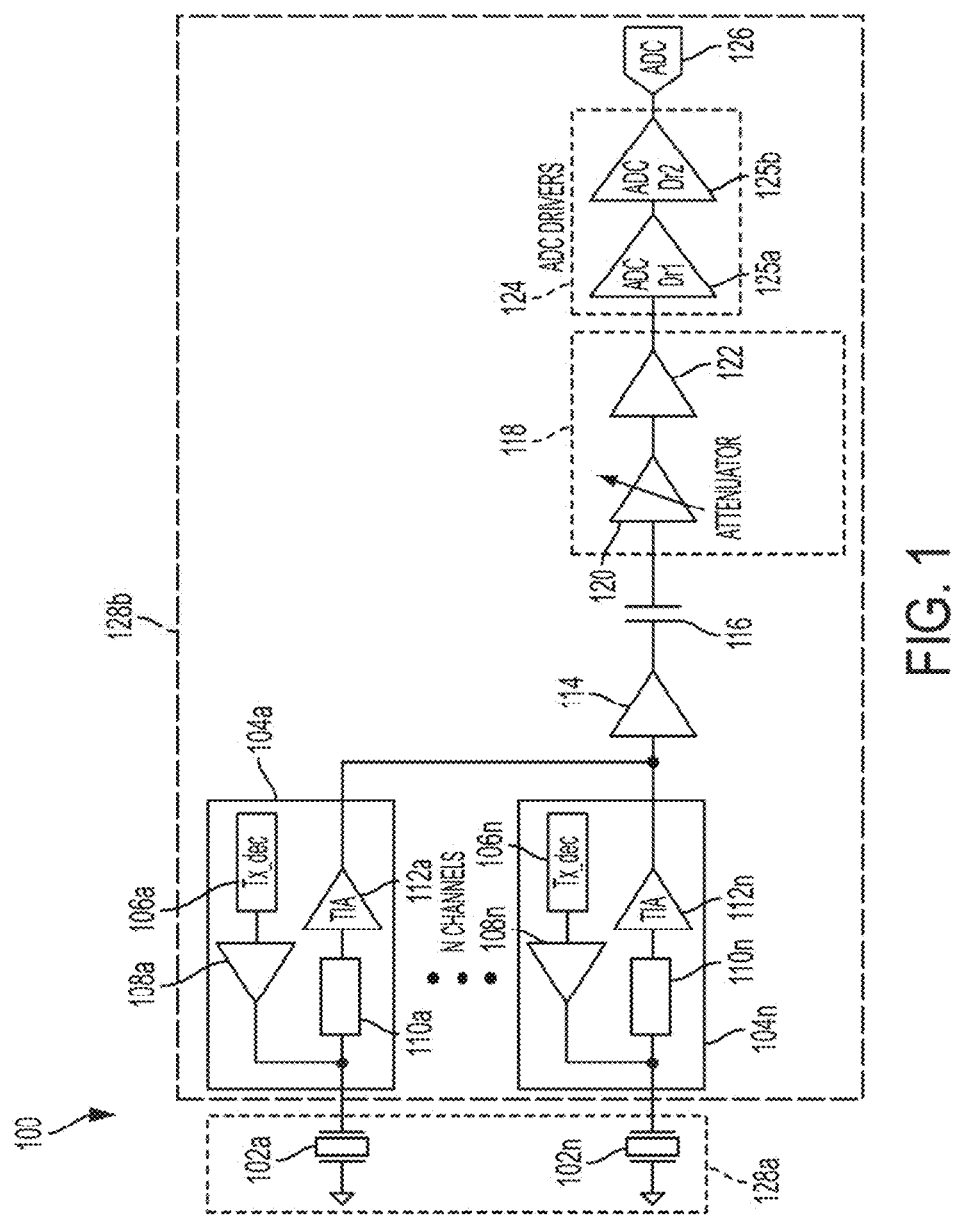
FIG. 1 is a block diagram of an ultrasound device including an analog-to-digital converter, according to a non-limiting embodiment of the present application.

FIG. 1 illustrates a circuit for processing received ultrasound signals, according to a non-limiting embodiment of the present application. The circuit 100 includes N ultrasonic transducers 102a . . . 102n, wherein N is an integer. The ultrasonic transducers are sensors in some embodiments, producing electrical signals representing received ultrasound signals. The ultrasonic transducers may also transmit ultrasound signals in some embodiments. The ultrasonic transducers may be capacitive micromachined ultrasonic transducers (CMUTs) in some embodiments. The ultrasonic transducers may be piezoelectric micromachined ultrasonic transducers (PMUTs) in some embodiments. Further alternative types of ultrasonic transducers may be used in other embodiments.

The circuit 100 further comprises N circuitry channels 104a . . . 104n. The circuitry channels may correspond to a respective ultrasonic transducer 102a . . . 102n. For example, there may be eight ultrasonic transducers 102a . . . 102n and eight corresponding circuitry channels 104a . . . 104n. In some embodiments, the number of ultrasonic transducers 102a . . . 102n may be greater than the number of circuitry channels.

The circuitry channels 104a . . . 104n may include transmit circuitry, receive circuitry, or both. The transmit circuitry may include transmit decoders 106a . . . 106n coupled to respective pulsers 108a . . . 108n. The pulsers 108a . . . 108n may control the respective ultrasonic transducers 102a . . . 102n to emit ultrasound signals.

The receive circuitry of the circuitry channels 104a . . . 104n may receive the electrical signals output from respective ultrasonic transducers 102a . . . 102n. In the illustrated example, each circuitry channel 104a . . . 104n includes a respective receive switch 110a . . . 110n and an amplifier 112a . . . 112n. The receive switches 110a . . . 110n may be controlled to activate/deactivate readout of an electrical signal from a given ultrasonic transducer 102a . . . 102n. More generally, the receive switches 110a . . . 110n may be receive circuits, since alternatives to a switch may be employed to perform the same function. The amplifiers 112a . . . 112n may be trans-impedance amplifiers (TIAs).

The circuit 100 further comprises an averaging circuit 114, which is also referred to herein as a summer or a summing amplifier. In some embodiments, the averaging circuit 114 is a buffer or an amplifier. The averaging circuit 114 may receive output signals from one or more of the amplifiers 112a . . . 112n and may provide an averaged output signal. The averaged output signal may be formed in part by adding or subtracting the signals from the various amplifiers 112a . . . 112n. The averaging circuit 114 may include a variable feedback resistance. The value of the variable feedback resistance may be adjusted dynamically based upon the number of amplifiers 112a . . . 112n from which the averaging circuit receives signals. The averaging circuit 114 is coupled to an auto-zero block 116.

The auto-zero block 116 is coupled to a time gain compensation circuit 118 which includes an attenuator 120 and a fixed gain amplifier 122. Time gain compensation circuit 118 is coupled to an analog-to-digital converter (ADC) 126 via ADC drivers 124. In the illustrated example, the ADC drivers 124 include a first ADC driver 125a and a second ADC driver 125b. The ADC 126 digitizes the signal(s) from the averaging circuit 114.

According to aspects of the present application ADC 126 may be a successive approximation ADC. Successive approximation ADCs convert continuous analog waveforms into digital representations by performing a binary search through all possible quantization levels. In some embodiments, an asynchronous successive approximation ADC is used.

While FIG. 1 illustrates a number of components as part of a circuit of an ultrasound device, it should be appreciated that the various aspects described herein are not limited to the exact components or configuration of components illustrated. For example, aspects of the present application relate to the successive approximation ADC 126.

The components of FIG. 1 may be located on a single substrate or on different substrates. For example, as illustrated, the ultrasonic transducers 102a . . . 102n may be on a first substrate 128a and the remaining illustrated components may be on a second substrate 128b. The first and/or second substrates may be semiconductor substrates, such as silicon substrates. In an alternative embodiment, the components of FIG. 1 may be on a single substrate. For example, the ultrasonic transducers 102a . . . 102n and the illustrated circuitry may be monolithically integrated on the same semiconductor die. Such integration may be facilitated by using CMUTs as the ultrasonic transducers.

According to an embodiment, the components of FIG. 1 form part of an ultrasound probe. The ultrasound probe may be handheld. In some embodiments, the components of FIG. 1 form part of an ultrasound patch configured to be worn by a patient.

Figure 2:
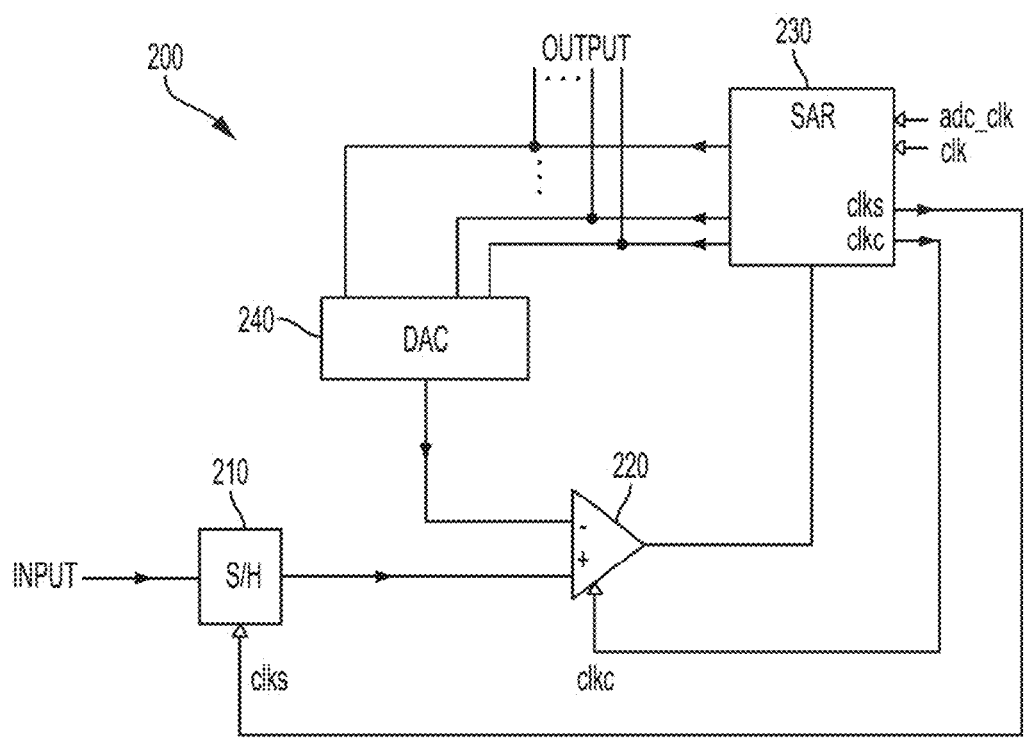
FIG. 2 is a block diagram of an asynchronous successive approximation analog-to-digital converter, according to a non-limiting embodiment of the present application.

FIG. 2 illustrates successive approximation ADC 200, according to aspects of the present application. The ADC may comprise a sample-and-hold circuit 210, a comparator 220, a digital-to-analog-converter (DAC) 240 and successive approximation register (SAR) controller 230. The output of the ADC is a digital representation of the input analog signal comprising of a word of N bits. N may have any value between 5 and 20.

According to aspects of the present application, the analog-to-digital conversion performed by ADC 200 is an iterative process. In each iteration the digital representation of the analog input voltage may be further improved by successively decreasing an error signal. Furthermore, ADC 200 may operate in an asynchronous fashion, such that each iteration is triggered by the completion of the previous iteration.

In some embodiments, ADC 200 may be coupled to one ultrasound transducer of a M×N array of ultrasound transducers, where M and N may assume any suitable value. In some other embodiments, a single transducer may be coupled to a plurality of circuits of the same type as ADC 200. In yet some other embodiments, ADC 200 may be fed by a signal that is obtained by combining the signals transduced by a plurality of ultrasound transducers.

According to aspects of the present application, in successive approximation ADC 200, the conversion is performed one bit at a time, starting from the most significant bit (MSB) to the least significant bit (LSB). Accordingly, the conversion of the $i^{th}$ bit of the sequence occurs at a non-predefined time and is triggered by the completion of the conversion of the $i-1^{th}$ bit. By way of explanation, the timing associated with the conversion of each bit is not governed by a clock signal, as it would be the case for synchronous successive approximation ADCs.

In some embodiments, the conversion of one bit is synchronous and is triggered by a clock signal, while all the other bits are asynchronous. In some embodiments, the most significant bit is the synchronous bit. In other embodiments, at least two bits, but not all bits, are synchronous while all the other bits are asynchronous.

Sample-and-hold (S/H) circuit 210 may be configured to receive an analog input signal. Sample-and-hold 210 may be single-ended or differential. During a specified period of time, sample-and-hold circuit 210 may capture a portion of the voltage associated with the input signal. Subsequently, sample-and-hold 210 may hold the captured voltage to a constant value. In some embodiments, sample-and-hold 210 may comprise a switch and a capacitor (not shown). During the sample phase, the switch may be in a "closed" state thus connecting the input voltage to the capacitor. In this phase, the input voltage may charge or discharge the capacitor for as long as the switch stays "closed". In the hold phase, the switch may be in an "open" state thus disconnecting the input voltage from the capacitor. The charge stored in the capacitor throughout the sample phase may result in a voltage across the capacitor that is proportional to the input voltage. During this phase, the capacitor may maintain the captured voltage at a constant level. However, the capacitor may be charged or discharged by its own leakage currents and consequently the stored voltage may change over time. Signal clks may be used to determine whether the switch of sample-and-hold 210 is in "closed" or "open" state. In some embodiments, when clks is equal to a logic 1 the switch is "closed" and when clks is equal to a logic 0 the switch is "open". However, the opposite logic may also be implemented. In some embodiments, the switch may be one or a combination of field effect transistors (FET), bipolar junction transistors (BJT) or any other suitable types of transistor. Furthermore, in some embodiments, the switch may follow an operational amplifier configured as a buffer amplifier to charge and discharge the capacitor.

The voltage acquired by sample-and-hold circuit 210 may be sent to one input port of comparator 220. The second input port of comparator 220 may be connected to the output of DAC 240. In some embodiments, if the acquired voltage is greater than the DAC output voltage, then comparator 220 may output a voltage corresponding to a "high" level or logic 1. Contrarily, if the DAC output voltage is greater than the acquired voltage, then comparator 220 may output a voltage corresponding to a "low" state or logic 0. However, any other suitable logic may be implemented. In some embodiments, comparator 220 may comprise an operational amplifier. In some embodiments, comparator 220 may be gated by signal clkc. In the "gated" state, comparator 220 may be configured to perform a comparison and output a voltage based on the input signals. In the "ungated" state, comparator 220 is not active and does not perform any comparison. In some embodiments, when clkc is equal to a logic 1 comparator 220 is gated and when clkc is equal to a logic 0 comparator 220 is ungated. However, the opposite logic may also be implemented.

Logic states 0 and 1 may represent any voltage as long as the voltage or voltage range corresponding to a logic 0 is different from the voltage or voltage range corresponding to a logic 1. In some embodiments, logic 1 corresponds to 1.8V and logic 0 corresponds to 0V. In some embodiments, logic 1 corresponds to any voltage between 0.5V and 5, and logic 0 corresponds to any voltage between −5V and 1V, such that the two ranges do not overlap.

According to aspects of the present application, successive approximation register (SAR) controller 230 may comprise one or more registers and a logic circuit. One of the registers may store the most recent digital representation of the analog input voltage. The content of the register may be continuously updated based on the result of the comparison performed by comparator 220. The digital word contained in the register may be transferred to DAC 230 that, in turn, may perform a digital-to-analog conversion. In some embodiments, the initial state of the register prior to the beginning of the analog-to-digital conversion may be set such that the most significant bit (MSB) is set to 1 while all the other bits are set to 0. In this scenario, DAC 240 may output an analog signal equal to Vref/2, where Vref is the reference voltage applied to DAC 240. However, any other suitable initial state may be implemented. In some embodiments, DAC 240 may be configured to output Vref when a digital word containing all 1s is received and may be further be configured to output 0V when a digital word containing all 0s is received. In some embodiments, DAC 240 comprises a charge distribution circuit. DAC 240 may further comprise a bank of capacitors disposed in a single-ended or differential configuration.

In some embodiments, the output digital representation may be configured to be equal to the input to DAC 240 as illustrated in FIG. 2. In some embodiments, the output digital representation may be stored in a dedicated register of SAR controller 230.

According to aspects of the present application, the analog-to-digital conversion performed by ADC 200 is an iterative process. In each iteration the digital representation of the analog input voltage is further improved by successively decreasing an error signal equal to the difference between the input signal and the DAC output signal.

The logic circuit of SAR controller 230 may be configured to sequentially scan through each bit of the N bits forming the digital representation of the analog input voltage. In some embodiments, during the first iteration the most significant bit is determined based on the result of the comparison performed by comparator 220. By way of example, if the output of the comparison is a logic 1, corresponding to a scenario in which the acquired signal is greater than the DAC output signal, the most significant bit (MSB) of the shift register is set to 1. Once the state of the MSB is determined the logic circuit skips to the following bit. The process continues until the least significant bit (LSB) is determined.

ADC 200 may operate in an asynchronous fashion, according to aspects of the present application. Each iteration may be triggered by the completion of the previous iteration. Control signals clks and clkc may be generated by the logic circuit of SAR controller 230 in response to clock signal clk and signal adc_clk.

Figure 3:
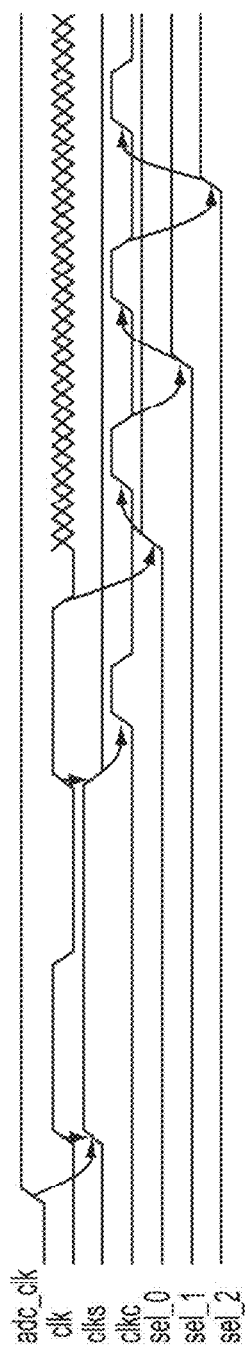
FIG. 3 is a graph illustrating the time evolution of seven control signals associated with the asynchronous successive approximation analog-to-digital converter of FIG. 2, according to a non-limiting embodiment of the present application.

FIG. 3 illustrates a non-limiting example of a timing diagram according to aspects of the present application. Signal adc_clk may be used to initialize the analog-to-digital conversion. In addition, clock signal clk may be provided to SAR controller 230. Clock signal clk may have a repetition rate between approximately 100 Hz and 10 GHz, between approximately 1 KHz and 100 MHz, between approximately 1 MHz and 50 MHz. In some embodiments, an edge of adc_clk, for example a rising edge, may initiate the conversion. Subsequently, an edge of clk, for example a rising edge, may trigger clks to switch to a logic 1. While clks is equal to 1, sample-and-hold circuit 210 may sample the analog input signal. Signal clks may remain in a 1 state for the duration of a clk cycle. In this case, when a second clk rising edge is provided, clks may return to 0. However, clks may remain in a 1 state for any suitable amount of time. In some embodiments, the second edge of clks, for example a falling edge, may trigger clkc to switch to a logic 1. While clkc is equal to 1, comparator 220 may compare the acquired signal to the DAC output signal. Signal clkc may remain in a 1 state for any suitable amount of time.

Each signal sel_i selects a bit of the register of SAR controller 230, where sel_0 selects the MSB and sel_N−1 selects the LSB. In some embodiments, when sel_i is set to 1, the $i^{th}$ bit of the register may be updated based on the result of the comparison performed by comparator 220. In some embodiments, the MSB may be triggered by clk, for example by a falling edge of clk. By way of example, sel_0 may switch to 1, when a falling edge of clk is provided. In some embodiments, all other bits except for MSB are triggered asynchronously. For example, when sel_0 is switched to 1, an edge of sel_0, for example a rising edge, may trigger a clkc pulse of any suitable duration, consisting of a rising edge followed by falling edge. The falling edge of clkc may in turn trigger sel_1 to switch to a 1 state. Similarly, sel_1 may trigger clkc which in turn may trigger sel_2. The methods may continue until the LSB is reached. The delay between successive bits may be tuned, for example by adjusting the duration of a clkc pulse. However, any other suitable technique to delay bits can be used.

According to aspects of the present application, clock signal clk may be used to trigger only a subset of the digital word. For example, clk may only trigger the MSB while all other bits may be triggered by the previous bit. Consequently, the requirements associated with the repetition rate of the clock signal may be relaxed compared to synchronous successive approximation ADC.

FIG. 3 shows a non-limiting example of how control signals clk_adc, clk, clks, clkc and sel_i, where i may assume any value between 0 and N−1, may be used to drive ADC 200. However, any other suitable control signal may be used, in substitution of or in addition to the aforementioned control signals. All control signals may be edge-triggered by either a rising edge or a falling edge, or may alternatively be pulse-triggered.

Figure 4:
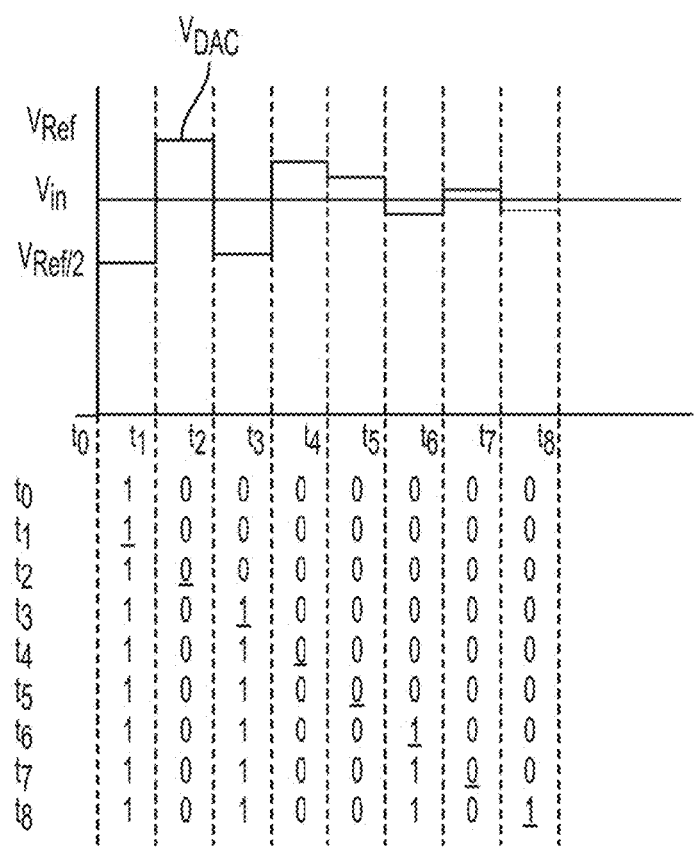
FIG. 4 is a graph illustrating the time evolution of a possible bit sequence as converted by the asynchronous successive approximation analog-to-digital converter of FIG. 2, according to a non-limiting embodiment of the present application.

By way of example, FIG. 4 shows a non-limiting analog-to-digital conversion of an input voltage $V_{in}$, according to aspects of the present application. In the non-limiting example, a 8-bit representation of the analog input voltage is provided. However, any number of bits may be used. In the non-limiting example, $V_{in}$ may exhibit a voltage between $V_{ref}$ and $V_{ref}/2$ and the ADC may be configured such that the initial DAC output voltage is set to $V_{ref}/2$. Accordingly, before the conversion is initiated at time t0, the value of the register may be equal to "10000000" where the first digit represents the MSB. Between $t_0$ and $t_1$, a comparison between $V_{in}$ and $V_{dac}$ may be performed, where $V_{dac}$ represents the DAC output voltage. In the non-limiting example, because $V_{in}$ is greater than $V_{dac}$, the MSB remains in a 1 state. The numeric table illustrated under the temporal chart, shows the content of the register after time $t_1$. The latest bit being updated is shown as underlined in the table. Between $t_1$ and $t_2$ a second comparison may be performed. In the non-limiting example, because $V_{dac}$ is greater than $V_{in}$, the second bit remains in a 0 state. Between $t_2$ and $t_3$ a third comparison may be performed. In the non-limiting example, because $V_{in}$ is greater than $V_{dac}$, the third bit is set to 1. The conversion may continue iteratively until the LSB is reached.

Figure 5:
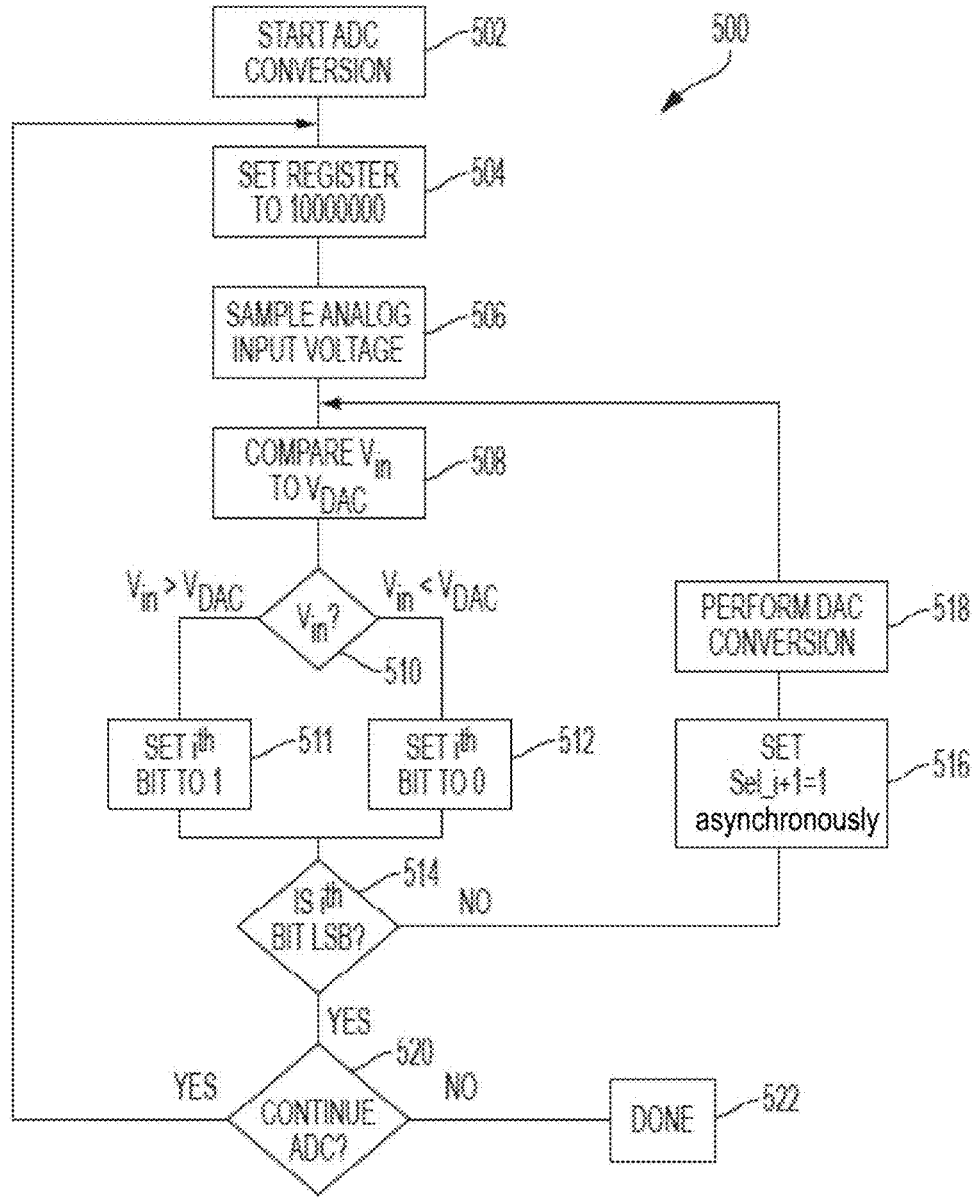
FIG. 5 illustrates the steps of a method to perform analog-to-digital conversion, according to a non-limiting embodiment of the present application.

FIG. 5 illustrates a method to perform a digital-to-analog conversion, according to aspects of the present application. Method 500 may start at step 502, for example when a rise edge of signal adc_clk is received by SAR controller 230. At step 504 the register may be set to "10000000". In the non-limiting example, the digital representation may be performed with an 8 bit-long word. However, any number of bits can be used. Regardless of the length of the register, the MSB may be set to 1 and all other bits may be set to 0. At step 506 an edge of clks may be received by sample-and-hold 210, and the analog input voltage may be sampled and stored. At step 508 comparator 220 may be gated through signal clkc triggered by an edge of clks. The triggering edge may be a falling edge. At step 510 comparator 220 may determine whether $V_{in}$ is greater than $V_{dac}$ or vice versa. In the former case, the $i^{th}$ bit may be set to 1, otherwise the $i^{th}$ bit may be set to 0. At step 514 SAR controller 230 may determine if the $i^{th}$ is the LSB. If the $i^{th}$ is not the LSB at step 516 the i+1$^{th}$ bit may be selected by setting sel_i+1 to 1. The selection of the i+1$^{th}$ bit may be performed asynchronously through an edge of clkc, as illustrated in FIG. 3. At step 518 a digital-to-analog conversion may be performed through DAC 240. Subsequently, method 500 may perform another iteration, and the updated value of $V_{dac}$ may be compared to $V_{in}$. Otherwise, if the $i^{th}$ bit is the LSB, the conversion of the sampled analog voltage may be completed. At step 520 the method determines if the analog-to-digital conversion is done. If the analog-to-digital conversion is not done, the method may continue from step 504, and a new sample of the analog input may be captured and converted.

Furthermore, the amount of time saved may be significant. In typical successive approximation analog-to-digital converters, the time necessary to perform a conversion may be limited by the repetition rate of the clock used to time the circuit. In some embodiments, utilizing an asynchronous successive approximation analog-to-digital converter of the types described herein may provide a substantial time saving by removing unnecessary idle period of times spent waiting for the subsequent clock edge. In some embodiments, utilizing an asynchronous successive approximation analog-to-digital converter of the types described herein may provide up to a 10% time saving, up to a 25% time saving, up to a 50% time saving, or any range or value within such ranges, in terms of the ADC.

In some embodiments, a plurality of successive-approximation-register (SAR) analog-to-digital converters (ADC) coupled to the ultrasonic transducer may be provided.

Having thus described several aspects and embodiments of the technology of this application, it is to be appreciated that various alterations, modifications, and improvements will readily occur to those of ordinary skill in the art. Such alterations, modifications, and improvements are intended to be within the spirit and scope of the technology described in the application. It is, therefore, to be understood that the foregoing embodiments are presented by way of example only and that, within the scope of the appended claims and equivalents thereto, inventive embodiments may be practiced otherwise than as specifically described.

As described, some aspects may be embodied as one or more methods. The acts performed as part of the method(s) may be ordered in any suitable way. Accordingly, embodiments may be constructed in which acts are performed in an order different than illustrated, which may include performing some acts simultaneously, even though shown as sequential acts in illustrative embodiments.

All definitions, as defined and used herein, should be understood to control over dictionary definitions, definitions in documents incorporated by reference, and/or ordinary meanings of the defined terms.

The phrase "and/or," as used herein in the specification and in the claims, should be understood to mean "either or both" of the elements so conjoined, i.e., elements that are conjunctively present in some cases and disjunctively present in other cases.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements.

As used herein, the term "between" used in a numerical context is to be inclusive unless indicated otherwise. For example, "between A and B" includes A and B unless indicated otherwise.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively.

What is claimed is:

1. An apparatus, comprising:
   at least one ultrasonic transducer;
   a plurality of asynchronous successive-approximation-register (SAR) analog-to-digital converters (ADCs) coupled to the at least one ultrasonic transducer, at least one asynchronous SAR ADC in the plurality having a sample and hold stage, a digital-to-analog converter (DAC), a comparator, and control circuitry,
   wherein a DAC update event of the at least one SAR ADC following at least one bit conversion is synchronized to a corresponding DAC update event of at least one other SAR ADC in the plurality of SAR ADCs, and
   wherein conversion of a next bit of the at least one SAR ADC after the at least one bit conversion is triggered by the DAC update event.

2. The apparatus of claim 1, wherein the at least one ultrasonic transducer comprises an M×N array of ultrasonic transducers.

3. The apparatus of claim 1, wherein the DAC update event is not synchronized to a system clock of the apparatus.

4. The apparatus of claim 1, wherein conversion of a most significant bit (MSB) of the at least one SAR ADC is synchronized to a system clock or a sampling clock of the apparatus.

5. The apparatus of claim 4, wherein conversion of bits of the at least one SAR ADC other than the MSB are not synchronized to the system clock of the apparatus.

6. The apparatus of claim 4, wherein conversion of at least two bits, but not all bits, of the SAR ADC is synchronized to the system clock or the sampling clock of the apparatus.

7. The apparatus of claim 1, wherein conversion of more than one bit, but not all bits of the at least one SAR ADC, is synchronous.

8. A method of operating an ultrasound device having a plurality of ultrasonic transducers and a plurality of asynchronous successive-approximation-register (SAR) analog-to-digital converters (ADCs), each ultrasonic transducer being respectively coupled to a SAR ADC, each asynchronous SAR ADC in the plurality having a sample and hold stage, a digital-to-analog converter (DAC), a comparator, and control circuitry, the method comprising:
   converting, in response to a first clock signal, a first bit of one SAR ADC in the plurality of SAR ADCs;
   updating a DAC in the one SAR ADC in response to the converting; and
   updating a DAC in another SAR ADC in the plurality of SAR ADCs in response to the updating a DAC in the one SAR ADC.

9. The method of claim 8, wherein the first clock signal is a system clock.

10. The method of claim 8, wherein a clock rate of the first clock signal is approximately a sampling frequency.

11. The method of claim 8, further comprising converting additional bits of the one SAR ADC in addition to the first bit of the one SAR ADC in response to the updating the DAC.

12. The method of claim 8, wherein conversion of at least two bits, but not all bits, of the one SAR ADC is synchronized to the first clock signal.

* * * * *